United States Patent
Bourne et al.

(10) Patent No.: US 10,294,934 B2
(45) Date of Patent: *May 21, 2019

(54) OPHTHALMIC LUBRICATION SYSTEM AND ASSOCIATED APPARATUS, SYSTEMS, AND METHODS

(71) Applicant: NOVARTIS AG, Basel (CH)

(72) Inventors: John Morgan Bourne, Irvine, CA (US); Glenn Robert Sussman, Laguna Niguel, CA (US)

(73) Assignee: Novartis AG, Basel (CH)

( * ) Notice: Subject to any disclaimer, the term of this patent is extended or adjusted under 35 U.S.C. 154(b) by 50 days.

This patent is subject to a terminal disclaimer.

(21) Appl. No.: 15/618,208

(22) Filed: Jun. 9, 2017

(65) Prior Publication Data

US 2017/0276127 A1    Sep. 28, 2017

Related U.S. Application Data

(63) Continuation of application No. 14/518,690, filed on Oct. 20, 2014, now Pat. No. 9,702,355.

(60) Provisional application No. 61/899,973, filed on Nov. 5, 2013.

(51) Int. Cl.
*F04B 43/08*     (2006.01)
*A61F 9/007*    (2006.01)

(52) U.S. Cl.
CPC ........ *F04B 43/086* (2013.01); *A61F 9/00736* (2013.01); *Y10T 29/4924* (2015.01)

(58) Field of Classification Search
CPC .......... A61M 5/14288; A61M 5/14236; A61M 1/0082; A61M 1/0084; A61M 3/0258; A61F 9/00736; F04B 43/084; F04B 43/086; F04B 43/088; F04B 43/09; F04B 43/12; F04B 43/1233

See application file for complete search history.

(56) References Cited

U.S. PATENT DOCUMENTS

| | | | |
|---|---|---|---|
| 2,015,123 A * | 9/1935 | Pennell | F04B 43/12 417/477.4 |
| 2011/0137231 A1* | 6/2011 | Sorensen | A61M 5/14228 604/22 |

FOREIGN PATENT DOCUMENTS

| | | |
|---|---|---|
| CN | 1133944 A | 10/1996 |
| CN | 102740905 A | 10/2012 |
| JP | 2009257179 A | 11/2009 |
| WO | 2014152376 A1 | 9/2014 |

* cited by examiner

*Primary Examiner* — Kenneth J Hansen

(57) ABSTRACT

Devices, systems, and methods including a lubricating solution bath for a pump integrated into an ophthalmic surgical hand piece are provided. In some embodiments, an ophthalmic pump system includes a housing defining a cavity. The system includes a rotating element positioned within the cavity of the housing. The system includes a flexible tubular structure positioned within the housing adjacent to the rotating element such that rotation of the rotation element urges a fluid through the flexible tubular structure. The system includes a lubricating solution positioned within the cavity around the rotating element and at least a portion of the flexible tubular structure.

13 Claims, 5 Drawing Sheets

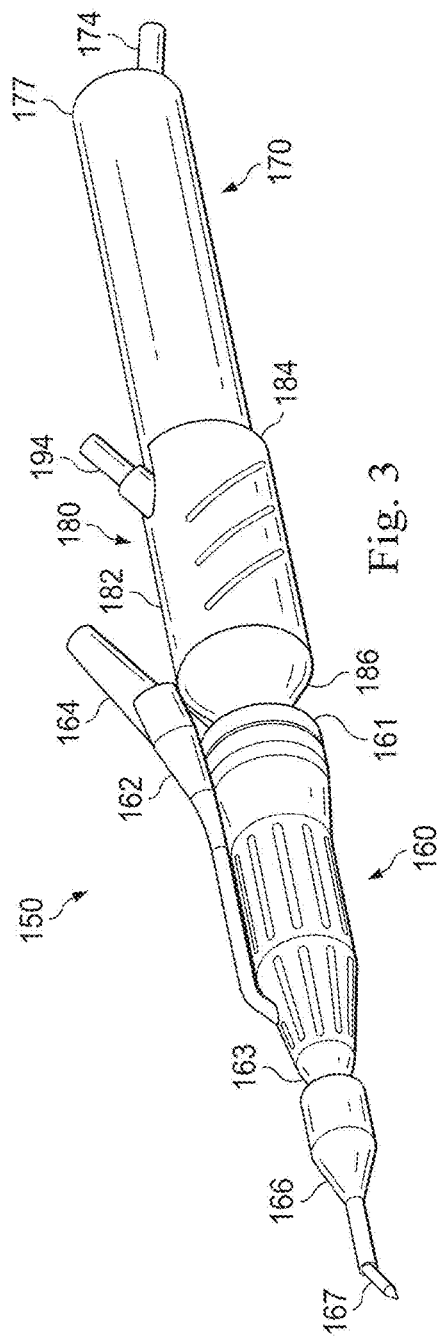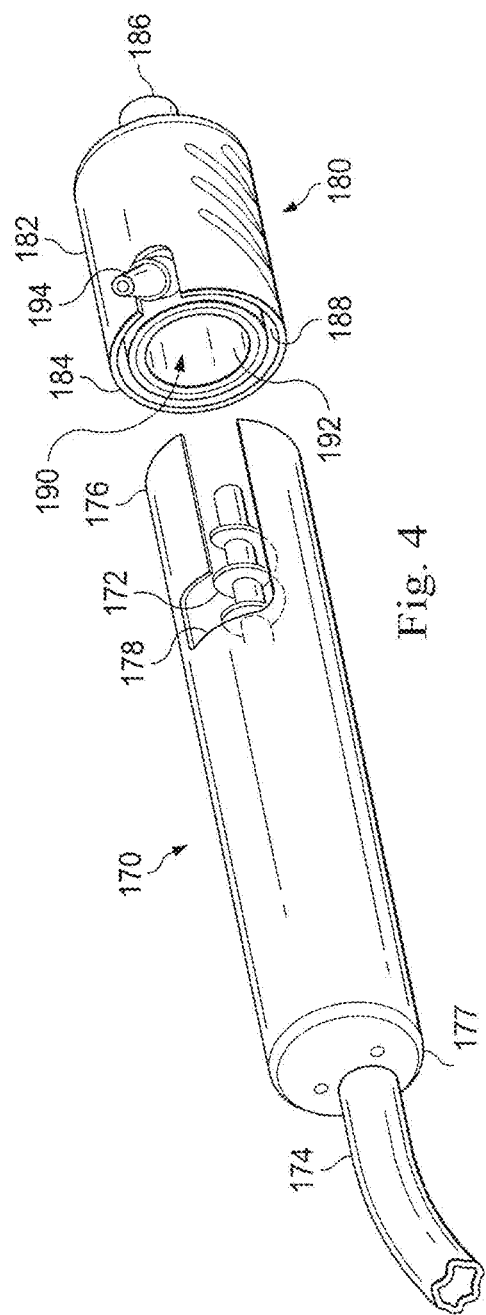

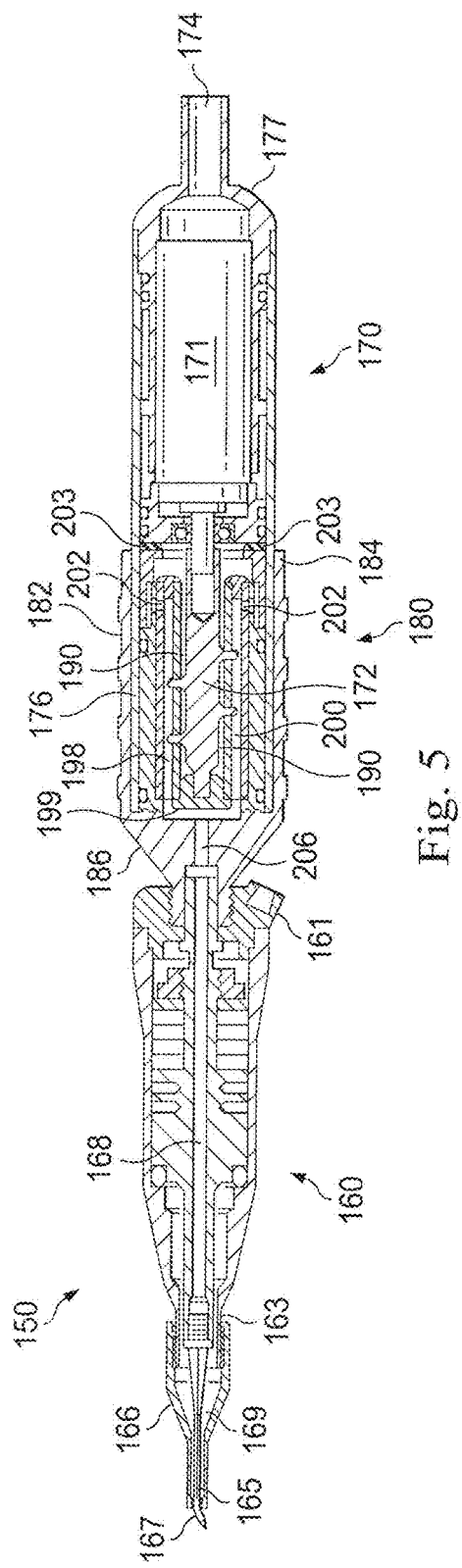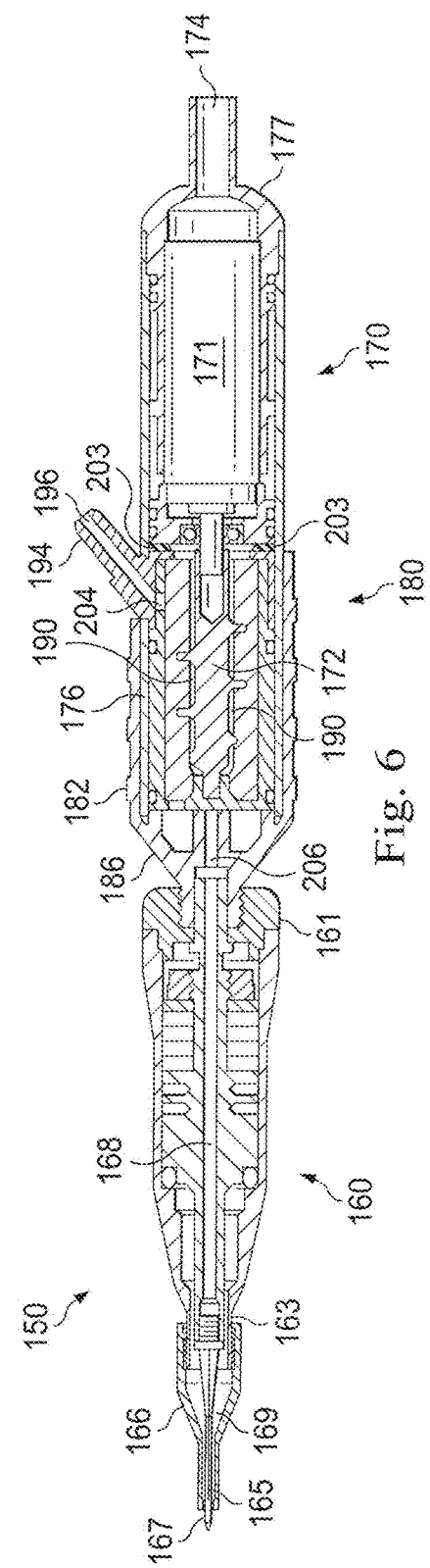

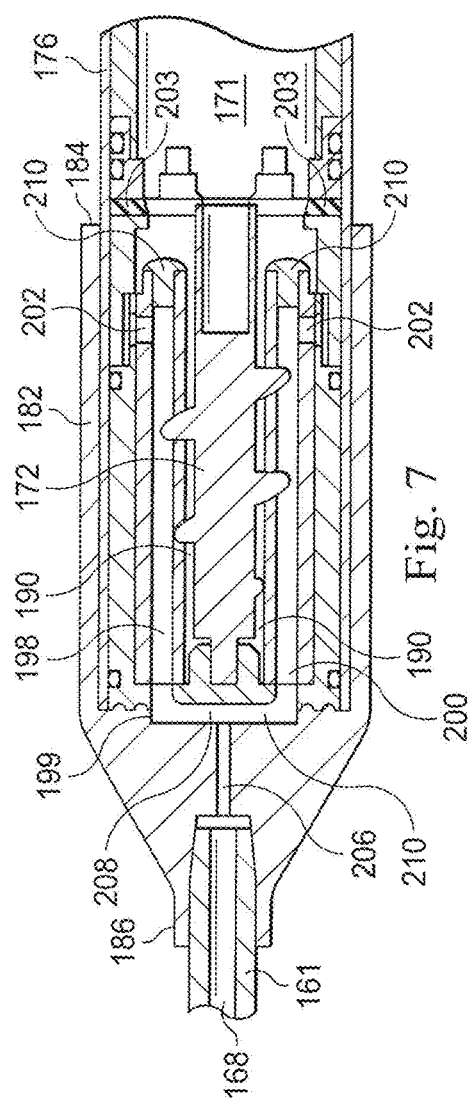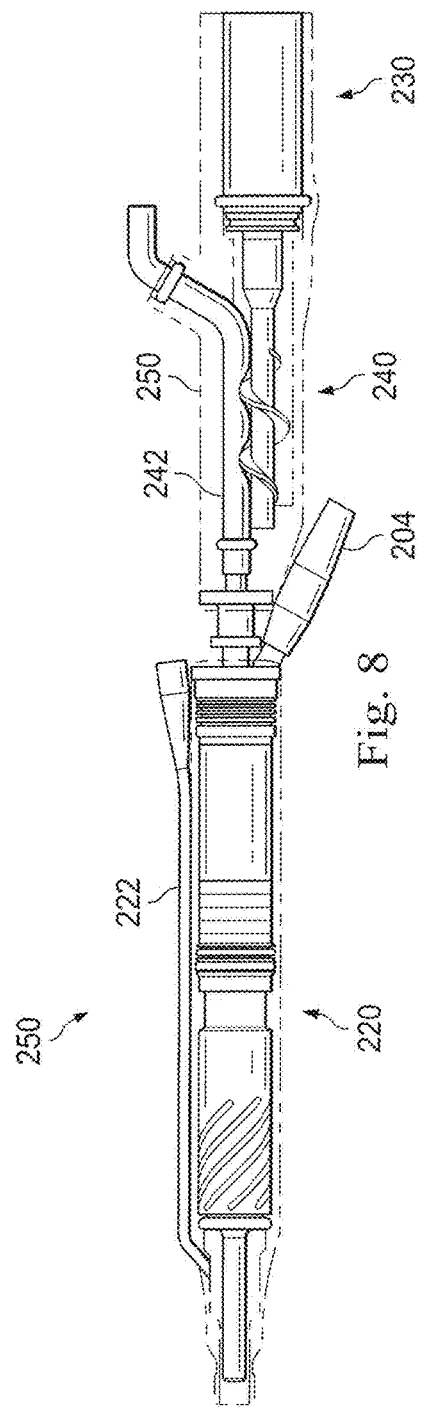

OPHTHALMIC LUBRICATION SYSTEM AND ASSOCIATED APPARATUS, SYSTEMS, AND METHODS

CROSS-REFERENCE TO RELATED APPLICATIONS

This application is a continuation of prior application Ser. No. 14/518,690, filed Oct. 20, 2014, and claims the benefit of U.S. Provisional Application No. 61/899,973, filed Nov. 5, 2013, the entire contents of each being incorporated herein by reference.

TECHNICAL FIELD

The devices, system, and methods disclosed herein relate generally to ophthalmic surgery, and more particularly, to a device that improves lubrication between components of an ophthalmic surgical hand piece.

BACKGROUND

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. A typical surgical hand piece suitable for phacoemulsification procedures consists of an ultrasonically driven phacoemulsification hand piece and an attached hollow cutting needle surrounded by an irrigating sleeve. During the phacoemulsification procedure, the tip of the cutting needle and the end of the irrigation sleeve are inserted into the anterior segment of the eye through a small incision in the outer tissue of the eye. The surgeon brings the tip of the cutting needle into contact with the lens of the eye, so that the vibrating tip fragments the lens. The resulting fragments are aspirated out of the eye through the cutting needle, along with irrigation solution provided to the eye during the procedure.

Challenges arise when pumps are integrated into the surgical hand piece to aspirate the lens fragments and irrigation solution away from the eye. For example, friction exists when one or more moving/rotating elements of the pump contact silicone tubing within the surgical hand piece. The silicon and/or other elastomeric tubing utilized in pumps is sufficiently tacky such that the tubing places a heavy torque load on a motor that is operating the pump. Thus, the motor can overheat or fail during use. One potential solution is to utilize a motor that can handle a heavier torque load. This, however, leads to a larger and heavier surgical hand piece, which can be difficult for a surgeon to operate, increases the chances of damage to the elastomeric tubing, and increases cost of the device. Other potential solutions such as exterior lubricating coating and/or self-lubricating silicon have been found to be ineffective and problematic because the lubricating material is stripped off of the tubing after a short period. Moreover, such solutions are generally implemented at the manufacturing stage, which increases the expense and reduces flexibility that an operator has prior to a surgical procedure.

SUMMARY

There remains a need for improved lubrication between an integrated surgical hand piece pump and elastomeric tubing contained in the surgical hand piece. The present disclosure addresses one or more deficiencies in the prior art. Embodiments disclosed herein are related to devices, systems, and methods that utilize a bath of lubricating solution to reduce friction associated with a pump integrated into an ophthalmic surgical hand piece.

Consistent with some embodiments, an ophthalmic pump system is provided. The ophthalmic pump system includes a housing defining a cavity. The ophthalmic pump system includes a rotating element positioned within the cavity of the housing. The ophthalmic pump system includes a flexible tubular structure positioned within the housing adjacent to the rotating element such that rotation of the rotation element urges a fluid through the flexible tubular structure. The ophthalmic pump system includes a lubricating solution positioned within the cavity around the rotating element and at least a portion of the flexible tubular structure.

The lubricating solution can include at least one of: balanced salt solution (BSS), balanced salt solution plus (BSS+), a viscoelastic solution, and sterile water. The flexible tubular structure can be at least partially disposed along a longitudinal axis of the housing. The flexible tubular structure can include a plurality of components at least partially distributed around the rotating element such that the rotating element is simultaneously in contact with more than one of the plurality of components. The plurality of components can include a first tubular element and a second tubular element, the first and the second tubular elements being symmetrically disposed around the housing. The plurality of components can include a central tubular element disposed at a distal portion of the housing, the central tubular element being in fluid communication with the first and the second tubular elements. The ophthalmic pump system can include a channel extending annularly around the housing, the channel being in fluid communication with the first and the second tubular elements. The ophthalmic pump system can include a projection extending obliquely from the housing, the projection including a lumen in fluid communication with the channel such that the fluid is transported away from the housing. The housing can be mechanically coupled to a surgical component such that the flexible tubular structure is in fluid communication with the surgical component, the surgical component aspirating the fluid from an eye of a patient. The surgical component can be a phacoemulsification component. The rotating element can be a scroll pump. The scroll pump can disposed in a pump component mechanically coupled to the housing.

Consistent with some embodiments, an ophthalmic lubrication kit for use with an ophthalmic surgical device is provided. The kit includes a housing defining a cavity. The cavity is configured to be filled with a lubricating solution and receive a rotating element. The housing includes a flexible tubular structure positioned in an interior thereof and configured to be adjacent the rotating element when the rotating element is received in the housing such that rotation of the rotation element urges a fluid through the flexible tubular structure. The kit includes a container of the lubricating solution.

The lubricating solution can include at least one of: balanced salt solution (BSS), balanced salt solution plus (BSS+), a viscoelastic solution, and sterile water. The flexible tubular structure can include a plurality of components at least partially positioned adjacent to the rotating element such that the rotating element is simultaneously in contact with more than one of the plurality of components. The flexible tubular structure can include a first tubular element and a second tubular element, the first and the second tubular elements being symmetrically disposed around the housing. The housing can further include a channel extending annularly around the housing, the channel being in fluid communication with the first and the second tubular elements. The housing can further include a projection extending from the housing, the projection including a lumen in fluid communication with the channel. The housing can be configured to be mechanically coupled to a surgical component such that the flexible tubular structure is in fluid communication with the surgical component.

Consistent with some embodiments, a method of assembling an ophthalmic pump system is provided. The method includes obtaining a housing including, in an interior thereof, a cavity and a flexible tubular structure. The method includes filling the cavity with a lubricating solution. The method includes
inserting a rotating element into the cavity filled with the lubricating solution such that the rotating element is positioned adjacent the flexible tubular structure. The method includes activating the rotating element such that rotation of the rotating element urges a fluid through the flexible tubular structure.

Consistent with some embodiments, a method for lubricating an ophthalmic pump system is provided. The method includes rotating a rotating element of a pump component to direct a fluid through a flexible tubular structure of a housing, the rotating element positioned within a cavity of the housing, wherein the flexible tubular structure is positioned within the housing adjacent to the rotating element. The method includes lubricating one or more elements of the pump component with a lubricating solution disposed within the cavity and in contact with at least a portion of the rotating element and at least a portion of the flexible tubular structure.

Additional aspects, features, and advantages of the present disclosure will become apparent from the following detailed description.

BRIEF DESCRIPTION OF THE DRAWINGS

The accompanying drawings illustrate embodiments of the devices and methods disclosed herein and together with the description, serve to explain the principles of the present disclosure.

FIG. 3 is a stylized illustration of a perspective view of an ophthalmic surgical hand piece.

FIG. 4 is a stylized illustration of a perspective view of a pump component and a lubrication component of an ophthalmic surgical hand piece.

FIG. 5 is a stylized illustration of a cross-sectional side view of an ophthalmic surgical device.

FIG. 6 is a stylized illustration of a cross-sectional top view of an ophthalmic surgical device.

FIG. 7 is a stylized illustration of a partial cutaway side view of an ophthalmic surgical device.

FIG. 8 is a stylized illustration of a perspective view of an ophthalmic surgical device.

Figure 1:
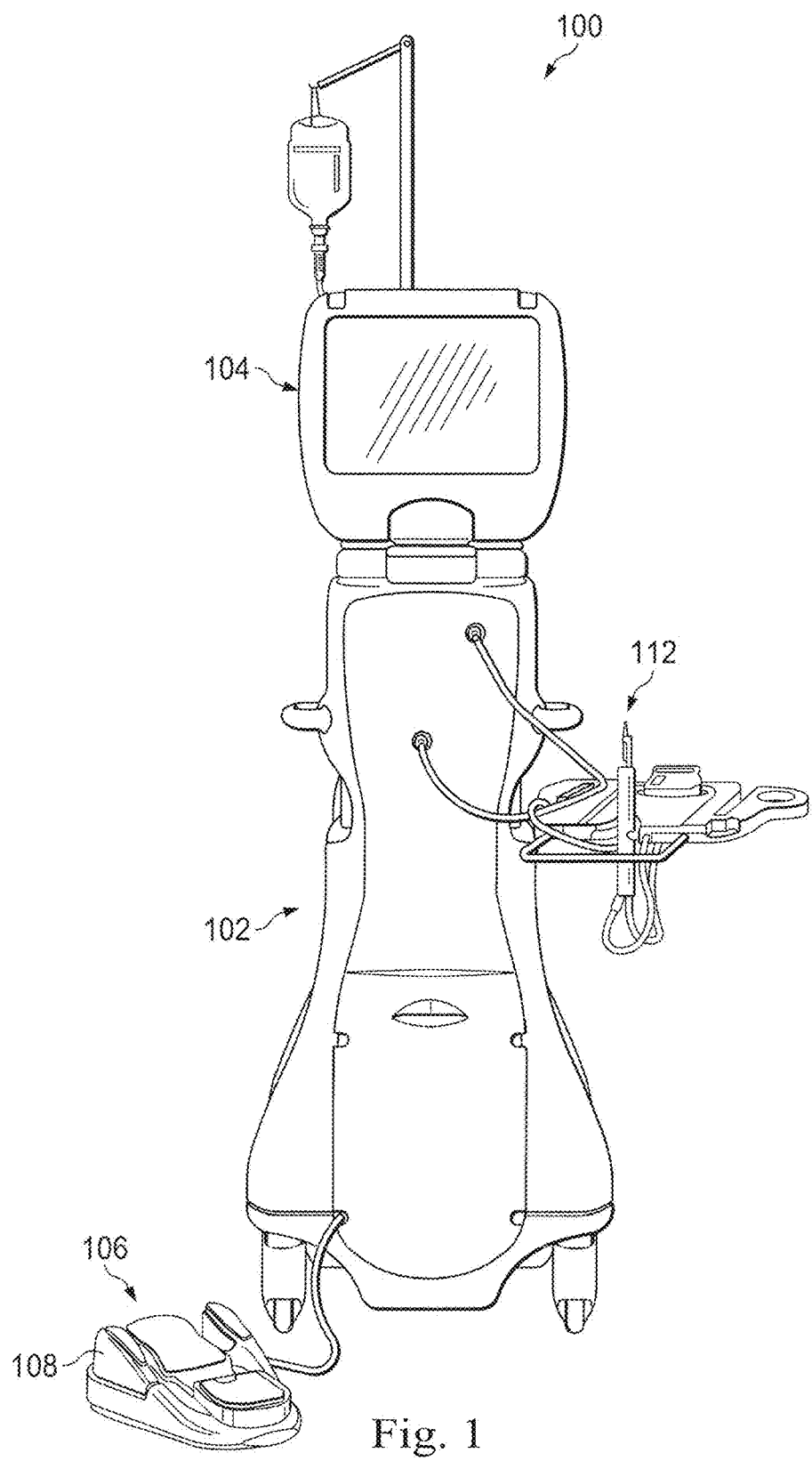
FIG. 1 is a stylized illustration of a front view an ophthalmic surgical console system.

In the drawings, elements having the same designation have the same or similar functions.

DETAILED DESCRIPTION

In the following description specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

In one or more aspects of the present disclosure, an ophthalmic surgical hand piece with an integrated pump utilizing a bath of lubricating solution is shown and described. The lubricating solution bath is provided in a consumable that is removably coupled to the portion of the hand piece including the pump. The consumable includes a housing defining a cavity that is filled with lubricating solution. Thus, the inner surface of the housing is in contact with the lubricating solution. The consumable also includes flexible tubing through which irrigating fluid and biological material (e.g., lens fragments) are aspirated away from the patient. When the consumable is coupled to the pump portion of the hand piece, a rotating element (e.g., a scroll, rollers, etc.) of the pump is received in the housing and is, thereby, surrounded by the lubricating solution. The flexible tubing is positioned within the cavity of the housing adjacent to the scroll pump such that rotation of the pump urges the fluid through the flexible tubing. The lubricating solution provides lubrication between the scroll pump and the flexible tubing when the scroll rotates and slides along the flexible tubing.

In one or more aspects of the present disclosure, the lubricating solution bath advantageously provides a superior reduction in motor load associated with the rotating scroll (due to reduced friction between the scroll and the flexible tubing). Reduced friction also advantageously enables an extended operating life for the surgical hand piece, the scroll, the motor, the flexible tubing, and/or other components of the surgical hand piece. In one or more aspects of the present disclosure, the lubricating solution bath provides continuous and lasting lubricating performance while the lubricating solution is held within the housing. Because the lubrication solution bath is an effective solution to reduce friction, other lubricating materials need not be used (e.g., on the exterior flexible tubing). Thus, cross-contamination of lubricating materials is advantageously avoided. In one or more aspects of the present disclosure, a fluid that is readily available during the surgical procedure (saline solution, sterile water, etc.) may be used as the lubricating solution. Thus, the lubricating solution may be added immediately prior to the surgical procedure by an operator (e.g., saline solution can be added from the irrigation supply line).

Figure 2:
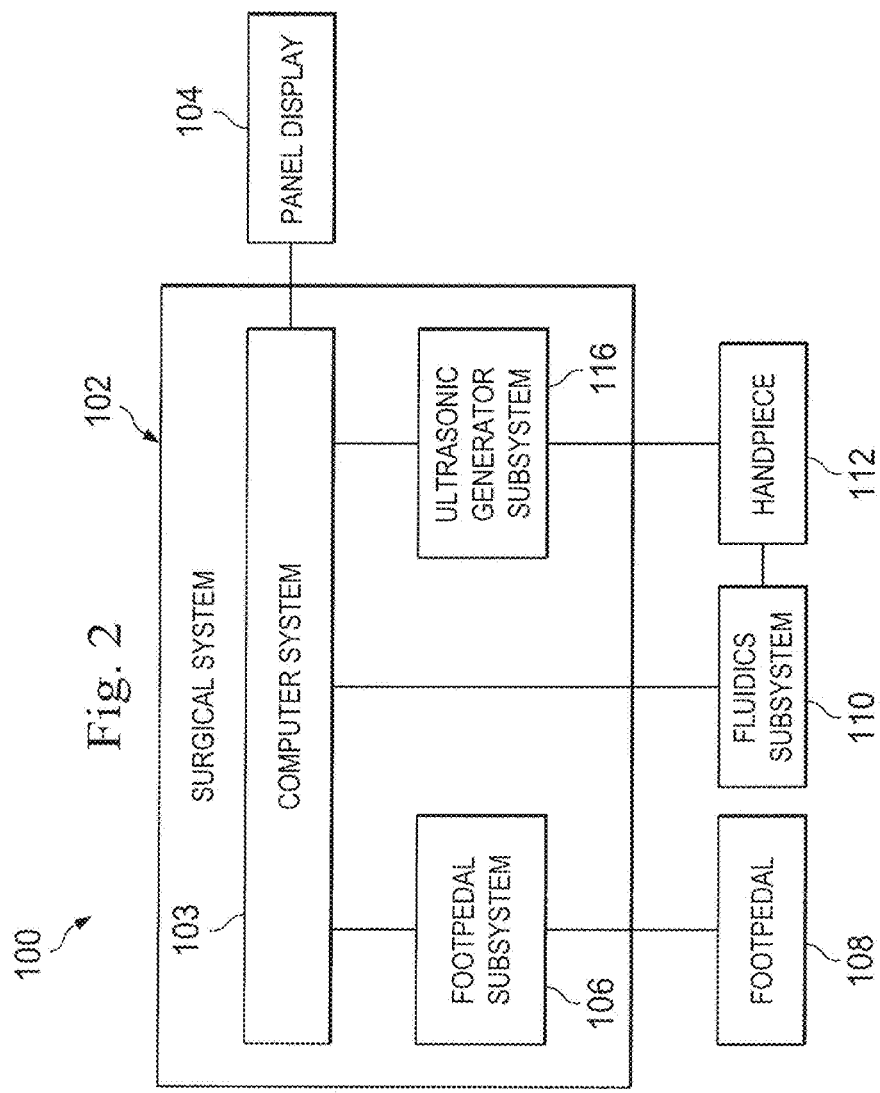
FIG. 2 is a block diagram of an ophthalmic surgical console system.

The discussion below generally refers to FIGS. 1 and 2. FIG. 1 is a stylized illustration of a front view an ophthalmic surgical console system 100. FIG. 2 is a block diagram of the console system 100, according to one embodiment of the disclosure. The console system 100 includes a base housing 102 with a computer system 103 and an associated display screen 104 showing data relating to system operation and performance during the surgical procedure. The console system 100 also includes at least a part of a number of subsystems, such as those shown in FIG. 2, that are used together to perform the surgical procedure. Some of these subsystems include components or elements that are separable from or not disposed on the housing 102. For example, the subsystems include a foot pedal subsystem 106 that includes, for example, a foot pedal 108 and an ultrasonic generator subsystem 116 that provides an ultrasonic oscillation to a cutting needle of the hand piece 112. In some embodiments, one or more components of fluidics subsystem 110 are disposed away from housing 102, including, e.g., an aspiration and/or irrigation pump that is integrated with the hand piece 112. In some embodiments, a drainage bag to receive aspirated fluid from the hand piece may be disposed away from hand piece 112 (e.g., on or near the console housing 102). Hand piece 112 itself may be integrally formed or include one or more separable components (as shown in, e.g., FIGS. 3-7). The subsystems may overlap and cooperate to perform various aspects of the procedure.

Surgical hand piece 112 can include an ultrasonically driven phacoemulsification hand piece and an attached hollow cutting needle surrounded by an irrigating sleeve. The hand piece 112 may be attached to the control housing 102 by an electric cable and flexible conduit. Through the electric cable, the console system 100 (e.g., the ultrasonic generator subsystem 116) varies the power level transmitted by the hand piece 112 to the attached cutting needle. The flexible conduit supplies irrigation fluid to the surgical site and draws aspiration fluid from the eye through the hand piece assembly.

The operative part in the hand piece 112 is a centrally located, hollow resonating bar or horn directly attached to a set of piezoelectric crystals. The crystals supply the required ultrasonic vibration needed to drive both the horn and the attached cutting needle during phacoemulsification, and are controlled by the console. The crystal/horn assembly may be suspended within the hollow body or shell of the hand piece by flexible mountings. The body of the hand piece 112 terminates in a reduced diameter portion or nosecone at the body's distal end. The nosecone can be externally threaded to accept the hollow irrigation sleeve, which surrounds most of the length of the cutting needle. Likewise, the horn bore can be internally threaded at its distal end to receive the external threads of the cutting tip. The irrigation sleeve may have an internally threaded bore that is screwed onto the external threads of the nosecone. The cutting needle can be adjusted so that its tip projects only a predetermined amount past the open end of the irrigating sleeve.

Throughout a phacoemulsification procedure, irrigating fluid is pumped into the eye, passing between the irrigation sleeve and the cutting needle, and exiting into the eye at the tip of the irrigation sleeve and/or from one or more ports, or openings, cut into the irrigation sleeve near its end. This irrigating fluid is critical, as it prevents the collapse of the eye during the removal of the emulsified lens. The irrigating fluid also protects the eye tissues from the heat generated by the vibrating of the ultrasonic cutting needle. Furthermore, the irrigating fluid suspends the fragments of the emulsified lens for aspiration from the eye.

A fluidics subsystem 110 can be provided on or away from the console housing 102 for aspirating the irrigating fluid along with lens fragments from the eye. When provided on the console housing 102, the fluidics subsystem 110 can include a fluidics cassette that pumps the irrigating fluid away from the eye through the surgical hand piece 112. A flexible conduit extends from the surgical hand piece 112 to the fluidics cassette at the console. In some embodiments, the surgical hand piece 112 includes an integrated aspiration pump. Such hand pieces move the fluidics subsystem 110 (e.g., the fluidics cassette) out of the console housing 102 and provide an aspirating pump in the surgical hand piece 112.

One common complication that can occur during the phacoemulsification process arises from a blockage, or occlusion, of the aspirating needle. As the irrigation fluid and emulsified tissue is aspirated away from the interior of the eye through the hollow cutting needle, and into a drain reservoir (e.g., provided at the console housing 102), pieces of tissue that are larger than the diameter of the needle's bore may become clogged in the needle's tip. While the tip is clogged, vacuum pressure builds up within the tip. The resulting drop in pressure in the anterior chamber in the eye when the clog is removed is known as post-occlusion surge. This post-occlusion surge can, in some cases, cause a relatively large quantity of fluid and tissue to be aspirated out of the eye too quickly, potentially causing the eye to collapse and/or causing the lens capsule to be torn. When an aspirating pump is provided in the surgical hand piece 112, the distance between the pump and the eye is reduced. Consequently, post-occlusion surges can be reduced and chamber stability in the interior chamber of the eye can be increased.

FIG. 3 is a stylized illustration of a perspective view of an ophthalmic surgical hand piece, according to one embodiment of the disclosure. Surgical hand piece 150 may be similar to surgical hand piece 112 of FIGS. 1 and 2. Surgical hand piece 150 may be fluidly, electrically, and/or otherwise coupled to other components of console system 100. For example, one or more electrical cables, flexible conduits, etc. may connect surgical hand piece 150 to console housing 102. Surgical hand piece 150 includes surgical component 160, pump component 170, and lubrication component 180. FIG. 3 shows surgical hand piece 150 as a modular assembly of separate components 160, 170, 180. In some embodiments, surgical hand piece 150 may be integrally formed, while still including components 160, 170, 180.

Surgical component 160 may include one or more elements for performing an ophthalmic surgical procedure on patient. In the embodiment of FIG. 3, surgical component 160 is a phacoemulsification hand piece. In other embodiments, surgical component 160 may be used for capsule polishing, etc. Surgical component 160 includes a proximal portion 161, a distal portion 163, an irrigating line connector 162, and an electrical connector 164. Electrical connector 164 may be removably coupled to an electrical cable to power one or more aspects of surgical component 160 (e.g., piezoelectric crystals) to cause, e.g., vibration of a phacoemulsification tip 167. Irrigating line connector 162 may be removably coupled to a flexible conduit that provides irrigating fluid to the surgical component. The fluid may be dispensed into the eye during the surgical procedure. Surgical component 160 includes phacoemulsification tip 167 at the distal portion 163. The phacoemulsification tip or needle 167 may be removably, mechanically coupled to the distal portion 163 of surgical component 160. An elastomeric sleeve 166 may be disposed annularly around phacoemulsification tip 167 and mechanically coupled to the distal portion 163 of surgical component 160. Phacoemulsification tip 167 may, e.g., vibrate and be in contact with the eye during the surgical procedure. Irrigating fluid and/or fragments of biological matter may be aspirated through phacoemulsification tip 167 into surgical component 160. For example, phacoemulsification tip 167 and surgical component 160 may each include central lumens through which fluid and/or biological matter is aspirated. The lumens may extend longitudinally along an entirety of phacoemulsification tip 167 and surgical component 160, respectively. In some embodiments, the lumens may be "central" in that they are coaxially disposed relative to phacoemulsification tip 167 and surgical component 160, respectively. In other embodiments all or some portion of the lumens may be offset from the center. The central lumens of phacoemulsification tip 167 and surgical component 160 may be aligned such that the phacoemulsification tip 167 and surgical component 160 are in fluid communication. The selective engagement of the phacoemulsification tip 167 and elastomeric sleeve 166 with the surgical component 160 allows phacoemulsification tip 167 and elastomeric sleeve 166 to be disposable components configured for use in a single procedure, while the surgical component 160 is a reusable component that can be sterilized (e.g., using autoclave procedures) and used in multiple procedures.

Pump component 170 may include one or more elements for drawing irrigating fluid and/or biological matter from the eye, through disposable tip 166, surgical component 160, and lubrication component 180. According to an exemplary embodiment, the one or more elements include a scroll and motor that operates the scroll. Electrical cable/connector 174 may be coupled to an electrical cable to provide power to the motor to operate the scroll. Pump component 170 may be removably coupled to lubrication component 180. For example, a distal portion of pump component 170 may be received in lubrication component 180.

Lubrication component 180 may include one or more elements to reduce friction between one or more other elements of lubrication component 180 and one or more elements of pump component 170, when such elements are in contact. In some embodiments, lubrication component 180 is a disposable component configured for use in a single procedure. Lubrication component 180 can be described as a consumable. In some embodiments, lubrication component 180 is a component that can be sterilized (e.g., using autoclave procedures) and used in multiple procedures. In some embodiments, lubrication component 180 is integrally formed with one or more other components (e.g., surgical component 160 and/or pump component 170). Lubrication component 180 includes a housing 182 that defines an interior cavity. The cavity may be filled with a lubricating solution. The lubricating solution may be self-filled (e.g., automatically, semi-automatically) as surgical hand piece 150 is assembled prior to the surgical procedure or manually filled by an end user prior to a surgical procedure. Lubrication component 180 also includes a flexible tubular structure. The flexible tubular structure is configured to carry irrigating fluid and/or biological material through lubrication component 180. In some embodiments, the flexible tubular structure includes multiple parts or sections. For example, the flexible tubular structure can include a unified section at a distal portion 186 and a bifurcated section extending along the length of the housing. One or more sections of the flexible tubular structure may be adjacent to the cavity with lubricating solution. In some embodiments, the flexible tubular structure may at least partially define an inner surface of the cavity. In other embodiments, the one or more sections of the flexible tubular structure are adjacent to a portion of the housing defining the cavity such that contact (e.g., by a rotating element of pump component 170) with the inner surface defining the cavity results in indirect contact with the tubular structure (e.g., through a flexible wall defining the cavity).

Distal portion 186 of lubrication component 180 may be coupled to the proximal portion 161 of surgical component 160. As described herein, a central lumen of surgical component 160 carries fluid and/or biological matter from the patient's eye. A section of the flexible tubular structure may be aligned with the central lumen of surgical component 160 such that surgical component 160 and lubrication component 180 are in fluid communication. Thus, fluid and/or biological matter may be carried from the patient's eye through to distal tip 166, surgical component 160, and lubrication component 180. Lubrication component 180 may include an aspiration projection 194, which may be removably coupled to a flexible conduit. Fluid and/or biological matter in lubrication component 180 may be evacuated away from the patient and/or surgical hand piece 150 via the flexible conduit coupled to aspiration projection 194. In some embodiments, aspiration projection 194 may include a Luer taper. However, it is understood that any type of selective engagement feature(s) or connectors can be utilized to couple aspiration projection 194 to a corresponding flexible conduit, including without limitation press fit, Luer lock, threads, and combinations thereof, among other connection types.

Lubrication component 180 is removably coupled to pump component 170. For example, a distal portion of pump component 170 may be received in a longitudinal groove extending around a perimeter and substantially along a length of lubrication component 180. When lubrication component 180 and pump component 170 are so coupled, a rotating element (e.g., scroll) of pump component 170 is received in the cavity defined by the housing of lubrication component 180. As described herein, the cavity is filled with the lubricating solution, and once inserted into the cavity, the rotating element is surrounded by the lubricating solution. Once inserted into the cavity, the rotating element is also positioned adjacent to one or more sections of the flexible tubular structure of the lubrication component 180. That is, at least some portions of the rotating element are directly or indirectly in contact with portions of the flexible tubular structure. Portions of the flexible tubular structure that are in contact with the rotating element may be temporarily deformed (e.g., until the rotating element is no longer in contact with that portion). One or more sections of the flexible tubular structure may be formed of a flexible, elastomeric, and/or resilient material (e.g., silicone).

The rotating element may function as a peristaltic-type pump to cause flow of irrigating fluid and/or biological material through distal tip 166, surgical component 160, and lubrication component 180. When caused to be rotated, the rotating element (e.g., scroll) slides along and squeezes portions of the flexible tubular structure. This causes the movement of a bolus of fluid along the flexible tubular structure. A vacuum is created in the wake of the moving bolus, which is filled by additional fluid. As rotation of the scroll continues, fluid and/or biological material are urged through the flexible tubular structure (e.g., toward aspiration projection 164 and away from surgical hand piece 150). In the embodiment of FIG. 3, fluid flow may be from left to right in surgical hand piece 150. In other embodiments, the rotating element may be operated such that fluid flows right to left in surgical hand piece 150. The selective engagement of the lubrication component 180 with the surgical component 160 and the pump component 170 allows lubrication component 180 to be a disposable component configured for use in a single procedure, while the surgical component 160 and the pump component 170 are reusable components that can be sterilized (e.g., using autoclave procedures) and used in multiple procedures.

FIG. 4 is a stylized illustration of a perspective view of a pump component and a lubrication component of an ophthalmic surgical hand piece, according to one embodiment of the disclosure. Pump component 170 includes a rotating element 172. In the embodiment of FIG. 4, rotating element 172 is a scroll. In other embodiments, rotating element 172 may be one or more other parts that are configured to be in contact with, apply force to, slide along, and/or squeeze various portions of the flexible tubular structure of the lubrication component 180. Because rotating element 172 is a scroll, multiple portions thereof may be simultaneously in contact with the flexible tubular structure. Rotating element 172 may be operated by a motor housed in pump component 170. The motor may be powered by electrical cable/connector 174, which is disposed at the proximal portion 177 of pump component 170. Pump component 170 is shown to be generally cylindrically shaped. In some embodiments, pump component 170 be shaped differently. Generally, the pump component 170 may have any shape, including those configured to facilitate grasping by an operator, coupling of various components, or otherwise improve the functionality or aesthetics of the device. A proximal portion 177 may be generally closed while a distal portion 176 may be generally open. Distal portion 176 includes a cutout 178. In some embodiments, cutout 178 is shaped similar to an elbow or the letter "L". Cutout 178 may include multiple sections including a longitudinal section and a transverse section. Cutout 178 may be differently shaped in other embodiments. Distal portion 176 may be received in a corresponding groove 188 of lubrication component 180.

Lubrication component 180 includes a housing 182. Housing 182 is shown to be generally cylindrically shaped. A proximal portion 184 is shown to be generally open. Distal portion 186 is shown to be tapered and generally closed. Distal portion 186 may be received in a surgical component to couple lubrication component 180 and the surgical component together. In some embodiments, lubrication component 180 may be shaped differently. Generally, the lubrication component 180 may have any shape, including those configured to facilitate grasping by an operator, coupling of various components, or otherwise improve the functionality or aesthetics of the device. Lubrication component 180 includes an aspiration projection 194 that extends away from housing 182 at an oblique angle. Aspiration projection 194 includes a lumen through which fluid and/or biological material is evacuated away from the patient and/or the surgical hand piece.

An interior of lubrication component 180 includes an inner surface 192 of housing 182, which defines a cavity 190. The portion or component of housing 182 defining the cavity 190 may be formed of a flexible, elastomeric, and/or resilient material. The portion or component of housing 182 defining the cavity 190 may also be formed of a rigid material, such as hard plastic or metal, in some instances. Cavity 190 may be filled with a lubricating solution before pump component 170 and lubrication component 180 are brought into engagement. In some embodiments, lubricating solution is a fluid that is readily available during the surgical procedure. For example, the lubricating solution may be one or more of a balanced salt solution (BSS), balanced salt solution plus (BSS+), a viscoelastic solution, and sterile water. In other embodiments, different fluids may be used. Lubrication component 180 includes groove 188, which may receive a distal portion 176 of pump component 170. Groove 188 may be annularly disposed around and/or extend around a perimeter of housing 182. Groove 188 may extend longitudinally along a substantial portion of lubrication component 180.

FIG. 4 shows pump component 170 and lubrication component 180 before they are brought into engagement or otherwise coupled. In some embodiments, distal portion 176 of pump component 170 is received in a groove 188 of lubrication component 180. When pump component 170 and lubrication component 180 are brought into engagement, distal portion 176 may be slid into groove 188 so that aspiration projection 194 lines up with the longitudinal section of cutout 178. Once the longitudinal section of the cutout 178 has been cleared, one or both of lubrication component 180 and pump component 170 may be rotated such that aspiration projection 194 is received in the transverse section of cutout 178. Once received in the transverse section of cutout 178, pump component 170 and lubrication component 180 are releasably locked together. Rotating element 172 may be received in cavity 190, which is filled with a lubrication solution. Rotating element 172 may be disposed adjacent to an inner surface 192 of housing 182 and/or portion of the flexible tubular structure of the lubrication component 180.

In some embodiments, the structures of pump component 170 and lubrication component 180 may be shaped differently, include additional and/or different features, etc., to facilitate coupling of the two components. For example, an interior surface of lubrication component may have threads, and an opposing surface of pump component 170 may have opposing threads. Lubrication component 180 and pump component 170 may be screwed together when brought into engagement. While FIG. 4 describes pump component 170 and lubrication component 180 as releasably coupled, in some embodiments, pump component 170 and lubrication component 180 may be integrally formed.

The discussion below generally refers to FIGS. 5, 6, and 7. FIG. 5 is a stylized illustration of a cross-sectional side view of an ophthalmic surgical device. FIG. 6 is a stylized illustration of a cross-sectional top view of the ophthalmic surgical device. FIG. 7 is a stylized illustration of a partial cutaway side view of the ophthalmic surgical device.

Surgical hand piece 150 includes surgical component 160, lubrication component 180, and pump component 170. Each component is disposed along a longitudinal axis of surgical hand piece 150. In some embodiments, lubrication component 180 may be longitudinally disposed between surgical component 160 and pump component 170. In other embodiments, the relative placement of the three components may be different. In the embodiment of FIGS. 5 and 6, surgical component is shown to be a phacoemulsification component. In some embodiments, surgical hand piece 150 includes more, fewer, and/or different components.

Surgical component 160 also includes one or more components associated with its performance of surgical tasks. For example, surgical component 160 may include piezoelectric crystals that cause vibration of a horn in the phacoemulsification component. Phacoemulsification tip or needle 167 may be mechanically coupled to the distal portion 163 of surgical component 160 and the vibrating horn, which in turn causes vibration of phacoemulsification tip 167. Irrigating fluid received through a flexible conduit coupled to irrigating line connector (e.g., irrigating line connector 162 of FIG. 1) can be provided into a patient's eye via an irrigating lumen 169 annularly disposed around phacoemulsification tip 167. The irrigating lumen 169 can extend between phacoemulsification tip 167 and the elastomeric sleeve 166, and longitudinally to a distal portion of phacoemulsification tip 167. The elastomeric sleeve 166 may be disposed annularly around phacoemulsification tip 167. Phacoemulsification tip 167 includes a central lumen 165 through which irrigating fluid and/or biological material is aspirated out of the eye. Surgical component 160 includes a central lumen 168 extending longitudinally along an entire length thereof. Central lumen 165 of phacoemulsification tip 167 is shown to be aligned with central lumen 168 of surgical component 160 such that phacoemulsification tip 167 and surgical component 160 are in fluid communication. Irrigating fluid and/or biological material received from the eye through central lumen 165 of phacoemulsification tip 167 travels through surgical component 160 and farther away from the eye via central lumen 168.

Proximal portion 161 of surgical component 160 is engaged with and/or otherwise coupled to distal portion 186 of lubrication component 180. Distal portion 186 of lubrication component 180 includes a tapered section, which is partially received in and which partially receives proximal portion 161 of surgical component 160.

Lubrication component 180 includes a flexible tubular structure, generally designated 199. Flexible tubular structure 199 carries irrigating fluid and/or biological material in lubrication component 180. Flexible tubular structure 199 includes multiple sections, including a central section 206 disposed in the distal portion 186. Central section 206 is aligned with central lumen 168 of surgical component 160 when the surgical component 160 is coupled with lubrication component 180. Thus, surgical component 160 and lubrication component 180 are in fluid communication. Central section 206 may be a unified section of flexible tubular structure 199. A bifurcated section of flexible tubular structure 199 may extend substantially along the length of lubrication component 180 between proximal portion 184 and distal portion 186. The bifurcated section may include flexible tubular components 198, 200. Having both flexible tubular components 198, 200 advantageously provides for improved flow capacity. It also allows the flexible tubular components to have a smaller cross-section, which advantageously allows other elements of lubrication component 180 to be properly fitted therein, lubrication component 180 to itself have a smaller cross-section, etc.

In some embodiments, flexible tubular components 198, 200 may be disposed opposite one another around rotating element 172 and/or housing 182. For example, the flexible tubular components 198, 200 are disposed approximately 180° apart from each other in the illustrated embodiment. In other embodiments, flexible tubular components 198, 200 may be disposed at angles greater than or less than 180° relative to each other. Flexible tubular components 198, 200 may be symmetrically disposed around housing 182. As shown in FIG. 7, central section 206 may divide into flexible tubular components 198, 200 via connecting tubular components 208, 210. Connecting tubular component 208, 210 are shown to each extend towards an exterior of lubrication component 180, in opposite directions relative to each other. Flexible tubular components 198, 200 extend longitudinally relative to connecting tubular components 208, 210. Connecting tubular component 208, 210 are shown to be disposed at right angles relative to central section 206 and flexible tubular components 198, 200. In other embodiments, connecting tubular components 208, 210 may be disposed at angles greater than or less than 90° relative to other sections of flexible tubular structure 199. Flexible tubular components 198, 200 in the bifurcated section of flexible tubular structure 199 may terminate at plugs 210 in the proximal portion 184. Plugs 210 may prevent the further displacement of fluid and/or biological material through flexible tubular structure 199.

The lubrication component 180 also includes a channel 202 that is at least partially annularly disposed around housing 182 and/or the longitudinal axis of lubrication component 180. Channel 202 may extend at least partially around a perimeter of housing 182. Once fluid and/or biological material has traveled from distal portion 186 to proximal portion 184 via flexible tubular components 198, 200, the fluid and/or biological material may proceed to channel 202 (because, e.g., plugs 210 prevent further longitudinal displacement). Channel 202 may extend towards an exterior of lubrication component 180 from flexible tubular components 198, 200. In other embodiments, channel 202 may extend towards an interior of lubrication component 180. Inlets to channel 202 from the flexible tubular components 198, 200 are disposed at right angles relative to flexible tubular components 198, 200 in the illustrated embodiment. In other embodiments, the inlets to channel 202 may be disposed at angles greater than or less than 90° relative to flexible tubular components 198, 200. Channel 202 may include a base 204 of a lumen 296 defined by aspiration projection 194. Base 204 may represent a location of lubrication component 180 at which fluid is joined at a single lumen after traversing a bifurcated section of flexible tubular structure 199. Thus, as the fluid is being aspirated from the patient's eye through surgical hand piece 150, the fluid may traverse through a single lumen, then be split across two or more lumens, and then recombined a single lumen. For example, the fluid may be aspirated from a patient's eye through disposable tip 166 to surgical component 160, then pass through central lumen 206, then be split between connecting tubular components 208, 210, travel along separate paths through flexible tubular components 198, 200, enter into two inlets of channel 202 from the flexible tubular component 198, 200, and finally be recombined and output from channel 202 into lumen 296 of projection 294.

FIGS. 5, 6, and 7 show pump component 170 engaged with and/or otherwise coupled to lubrication component 180. Distal portion 176 of pump component 170 may be received in a corresponding groove (e.g., groove 188 of FIG. 4) of lubrication component 180. Proximal portion 177 of pump component 170 includes an electrical cable/connector 174. Electrical cable/connector 174 provides power to motor 171, which is contained inside a housing of pump component 170. Motor 171 operates rotating element 172. In some embodiments, rotating element 172 is a scroll pump. In other embodiment, different pumps may be provided (e.g., rollers, etc.). A substantial portion and/or an entirety of rotating element 172 is disposed within a volume of lubrication component 180 when lubrication component 180 and pump component 170 are coupled. Rotating element 172 is positioned within the cavity (e.g., cavity 190 of FIG. 4) of lubrication component 180 that holds lubricating solution. Rotating element 172 is also positioned with the cavity such that rotating element 172 is adjacent the bifurcated section of flexible tubular structure 199. Portions of rotating element 172 may make contact with the inner surface of the housing (e.g., inner surface 192 of FIG. 4). An interior of the housing may be formed for a flexible, elastomeric, and/or resilient material. Because the bifurcated section of flexible tubular structure 199 (e.g., flexible tubular components 198, 200) is adjacent an inner surface of the housing when the rotating element 172 contacts an inner surface of the housing, flexible tubular structure 199 is also deformed by the contact. This may be described as indirect contact between the flexible tubular structure 199 and rotating element 172. In some embodiments, flexible tubular structure 199 may form at least part of the inner surface of the housing or be positioned within the cavity of the housing such that direct contact is made between flexible tubular structure 199 and rotating element 172.

In FIGS. 5 and 6, portions of flexible tubular components 198, 200 are shown to be deformed by contact of rotating element 172. Thus, advantageously, rotating element 172 makes contact directly or indirectly with tubular components 198, 200 while rotating element 172 is surrounded by lubricating solution and the inner surface of the housing (e.g., inner surface 192 of FIG. 4) is in contact with the lubricating solution. As rotating element 172 rotates, portions of rotating element 172 variously make contact with portions of flexible tubular components 198, 200. Because flexible tubular components 198, 200 are disposed 180° (e.g., symmetrically) from each other within housing 182 and around rotating element 172, rotating element 172 simultaneously contacts each of flexible tubular components 198 and 200. Rotation of rotating element 172 urges fluid and/or biological material through flexible tubular structure 199. Such urging of fluid in the lubrication component causes fluid to move from, e.g., disposable tip 166, through surgical component 160, to lubrication component 180, and away from the surgical hand piece 150 via a flexible conduit coupled to aspiration projection 194.

Lubrication component 180 can include a seal 203 configured to prevent undesired leaking of the lubricating solution from cavity 190. Seal 203 can be formed of an elastomeric material and extend annularly around lubrication component 180. When pump component 170 is coupled to lubrication component 180, pump component 170 can press against seal 203 such that seal 203 forms a barrier that prevents lubricating solution from leaking from cavity 190.

In use, an operator may assemble the ophthalmic pump system of surgical hand piece 150 described herein. In one embodiment, a housing 182 may be obtained. Housing 182 includes, in an interior thereof, a cavity 190 and a flexible tubular structure 199. An operator may fill the cavity 190 with a lubricating solution. An operator may then insert rotating element 172 into the cavity filled with the lubrication solution such that the rotating element is positioned adjacent the flexible tubular structure. For example, the operator may insert rotating element 172 into cavity 190 when the operator couples the lubrication component 180 and the pump component 170 to one another. An operator may activate the rotating element such that rotation of the rotating element urges a fluid through the flexible tubular structure. In some embodiments, the operator may further couple the housing 182 of the lubrication component 180 to the surgical component 160.

FIG. 8 is a stylized illustration of a perspective view of an ophthalmic surgical hand piece, according to one embodiment of the disclosure. Surgical hand piece 250 is similar to the surgical hand piece 150 (FIGS. 3, 5, and 6) in that surgical hand piece 250 includes a surgical component 220, lubrication component 240, and pump component 230. However, surgical hand piece 250 is different than surgical hand piece 150 in some respects. First, the flexible tubular structure 242 of lubrication component 240 is shown to be a single, unified structure (as opposed to a flexible tubular structure with different sections, including some sections that are unified and some sections that are bifurcated). Second, one or more components of surgical hand piece 250 may be integrally formed as opposed to being formed of individual modules (e.g., three modules corresponding to surgical component 220, lubrication component 232, and pump component 230) that are removably coupled. For example, lubrication component 240 and pump component 230 may be integrally formed and removably coupled to surgical component 220. Surgical component 220 includes an irrigation line connector 222 and an electrical cable/connector 264. Pump component 230 includes a rotating element 232. Lubrication component 240 includes a flexible tubular structure 242 through which fluid and/or biological material is aspirated away from surgical hand piece 250. A lubricating solution may be provided within a cavity defined by housing 250 of lubrication component 240. In some embodiments, the cavity of housing 250 may be filled with lubricating solution during manufacture of the pump component and/or lubrication component (e.g., when pump component 230 and lubrication component 240 are integrally formed). In other embodiments, cavity 250 may be manually filled by an operator prior to a surgical procedure. The surface of flexible tubular structure 242 may be in contact with the lubricating solution and rotating element 232 is surrounded by lubricating solution when rotating element 232 contacts flexible tubular structure 242.

Embodiments as described herein provide a lubricating solution bath for a rotating element of an integrated pump in an ophthalmic surgical hand piece. The lubricating solution bath reduces friction between a rotating element of the pump and a flexible tubular structure transporting fluid away from the patient's eye. The examples provided above are exemplary only and are not intended to be limiting. One skilled in the art may readily devise other systems consistent with the disclosed embodiments which are intended to be within the scope of this disclosure. As such, the application is limited only by the following claims.

The invention claimed is:

1. An ophthalmic pump system, comprising:
a housing defining a cavity;
a rotating element positioned within the cavity of the housing;
a plurality of flexible tubular components positioned within the housing adjacent to the rotating element such that rotation of the rotating element urges a fluid through the plurality of flexible tubular components; and
a lubricating solution positioned within the cavity around the rotating element and at least a portion of the plurality of flexible tubular components,
wherein the rotating element is simultaneously in contact with more than one of the plurality of flexible tubular components,
wherein the plurality of flexible tubular components includes a first tubular element and a second tubular element, the first and the second tubular elements being disposed around the housing, and
further comprising a channel extending annularly around the housing, the channel being in fluid communication with the first and the second tubular elements.

2. The ophthalmic pump system of claim 1, wherein the lubricating solution comprises at least one of: balanced salt solution (BSS), balanced salt solution plus (BSS+), a viscoelastic solution, and sterile water.

3. The ophthalmic pump system of claim 1, wherein at least a portion of the flexible tubular components extends along a longitudinal axis of the housing.

4. The ophthalmic pump system of claim 1, wherein the plurality of flexible tubular components includes a central tubular element disposed at a distal portion of the housing, the central tubular element being in fluid communication with the first and the second tubular elements.

5. The ophthalmic pump system of claim 1, further comprising a projection extending from the housing, the projection including a lumen in fluid communication with the channel.

6. The ophthalmic pump system of claim 1, wherein the housing is mechanically coupled to a surgical component such that the flexible tubular components are in fluid communication with a lumen of the surgical component.

7. The ophthalmic pump system of claim 6, wherein the surgical component is a phacoemulsification component.

8. The ophthalmic pump system of claim 1, wherein the rotating element is a scroll pump.

9. The ophthalmic pump system of claim 8, wherein the scroll pump is disposed in a pump component mechanically coupled to the housing.

10. An ophthalmic lubrication kit for use with an ophthalmic surgical device, the kit comprising:

a housing defining a cavity, the cavity configured to be filled with a lubricating solution and receive a rotating element, the housing including a plurality of flexible tubular components positioned in an interior thereof and configured to be adjacent the rotating element when the rotating element is received in the housing such that rotation of the rotating element urges a fluid through the plurality of flexible tubular components; and a container of the lubricating solution, wherein the plurality of components are at least partially positioned adjacent to the rotating element such that the rotating element is simultaneously in contact with more than one of the plurality of components, wherein the flexible tubular components include a first tubular element and a second tubular element, the first and the second tubular elements being disposed around the housing, and wherein the housing further comprises:

a channel extending annularly around the housing, the channel being in fluid communication with the first and the second tubular elements.

11. The ophthalmic lubrication kit of claim 10, wherein the lubricating solution comprises at least one of: balanced salt solution (BSS), balanced salt solution plus (BSS+), a viscoelastic solution, and sterile water.

12. The ophthalmic lubrication kit of claim 10, wherein the housing further comprises:

a projection extending from the housing, the projection including a lumen in fluid communication with the channel.

13. The ophthalmic lubrication kit of claim 10, wherein the housing is configured to be mechanically coupled to a surgical component such that the flexible tubular components are in fluid communication with the surgical component.

* * * * *